United States Patent
Timmer et al.

(10) Patent No.: US 8,053,746 B2
(45) Date of Patent: Nov. 8, 2011

(54) IRRADIATION DEVICE

(75) Inventors: Jan Hein Timmer, Cologne (DE); Holger Goebel, Nuembrecht (DE); Stefan Schmidt, Overath (DE); Juergen Heese, Cologne (DE); Michael Schillo, Bonn (DE)

(73) Assignee: Varian Medical Systems Particle Therapy GmbH, Bergisch-Gladbach (DE)

( * ) Notice: Subject to any disclaimer, the term of this patent is extended or adjusted under 35 U.S.C. 154(b) by 205 days.

(21) Appl. No.: 12/520,506

(22) PCT Filed: Apr. 5, 2007

(86) PCT No.: PCT/EP2007/003116
§ 371 (c)(1),
(2), (4) Date: Jun. 19, 2009

(87) PCT Pub. No.: WO2008/083721
PCT Pub. Date: Jul. 17, 2008

(65) Prior Publication Data
US 2009/0321665 A1 Dec. 31, 2009

(30) Foreign Application Priority Data
Dec. 21, 2006 (DE) .................... 20 2006 019 307 U

(51) Int. Cl.
*G01N 23/00* (2006.01)
(52) U.S. Cl. ............... 250/492.2; 250/492.1; 250/492.3; 250/397; 250/398; 378/10; 378/65; 378/143; 315/502

(58) Field of Classification Search ............... 250/492.1, 250/492.2, 492.3, 397, 398; 378/10, 65, 378/143; 315/502
See application file for complete search history.

(56) References Cited

U.S. PATENT DOCUMENTS

| | | |
|---|---|---|
| 3,925,676 A | 12/1975 | Bigham et al. |
| 3,955,089 A | 5/1976 | McIntyre et al. |
| 4,112,306 A | 9/1978 | Nunan |
| 4,507,616 A | 3/1985 | Blosser et al. |
| 4,641,104 A | 2/1987 | Blosser et al. |
| 4,870,287 A | 9/1989 | Cole et al. |
| 5,818,058 A | 10/1998 | Nakanishi et al. |
| 7,728,311 B2 * | 6/2010 | Gall .................... 250/492.21 |
| 2005/0089141 A1 | 4/2005 | Brown |

FOREIGN PATENT DOCUMENTS
DE  4411171  10/1995

OTHER PUBLICATIONS
ISA EPO; International Search Report of PCT/EP2007/003116; Jul. 4, 2007; 6 pages; NL.

* cited by examiner

*Primary Examiner* — David A Vanore
(74) *Attorney, Agent, or Firm* — Alleman Hall McCoy Russell & Tuttle LLP

(57) ABSTRACT

The present invention relates to an irradiation device for irradiating an irradiation object with heavy charged particles at an irradiation station, comprising a particle accelerator for providing a particle beam and a swivelling device for swivelling the particle beam impinging on the irradiation object, wherein the swivelling device comprises a carrier pivotable about an axis. In accordance with the invention, the irradiation device is characterized in that the particle accelerator is mounted on the pivotable carrier.

20 Claims, 4 Drawing Sheets

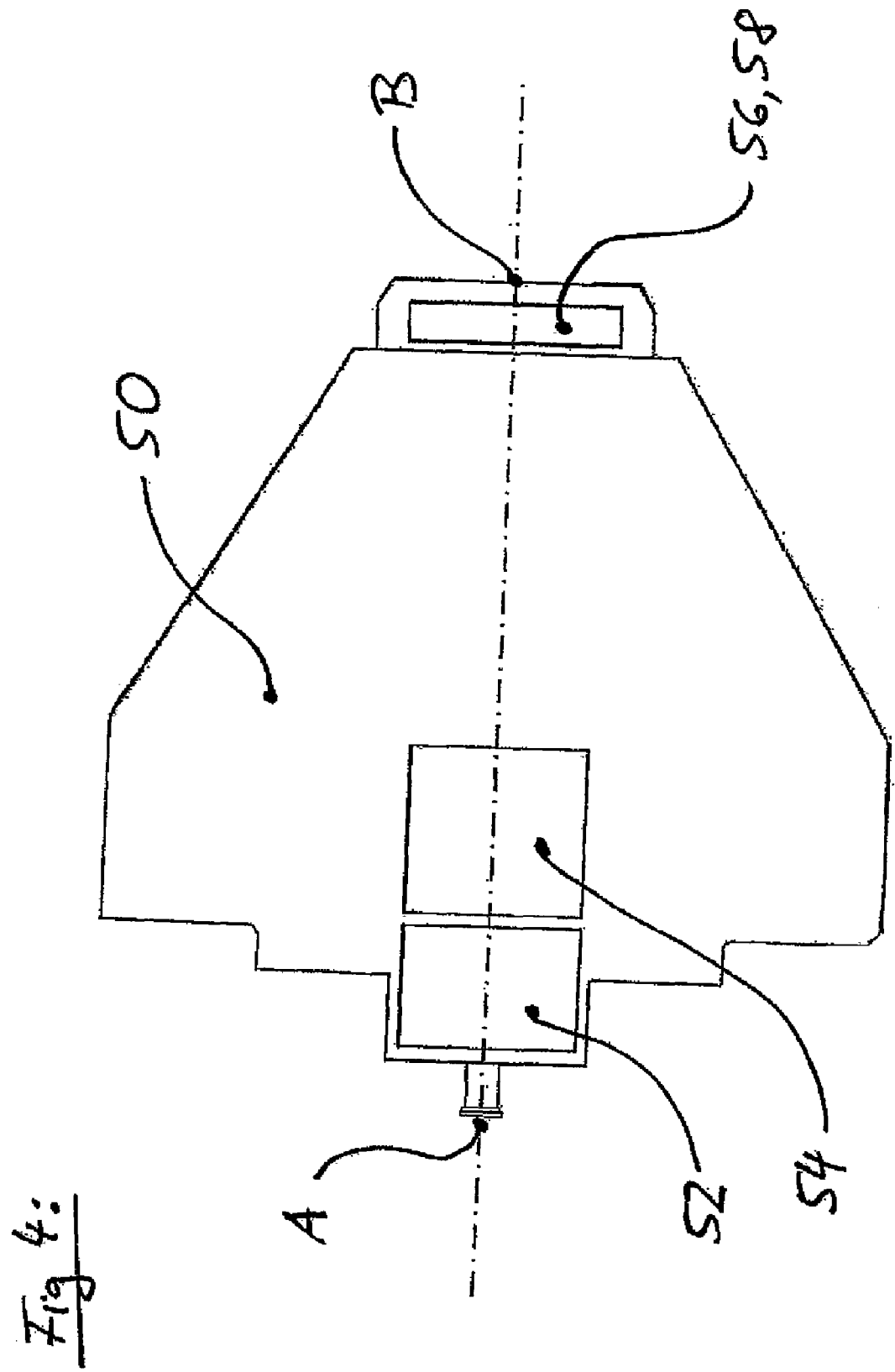

US 8,053,746 B2

IRRADIATION DEVICE

CROSS-REFERENCE TO RELATED APPLICATIONS

This is the U.S. National Phase of International PCT Application Serial No. PCT/EP2007/003116, filed Apr. 5, 2007, which claims priority to German Patent Application No. 20 2006 019 307.3, filed on Dec. 21, 2006, both of which are hereby incorporated by reference in their entirety for all purposes.

TECHNICAL FIELD

This invention relates to an irradiation device for irradiating an irradiation object with heavy charged particles, wherein the irradiation object is positioned at an irradiation station and is then irradiated with a particle beam impinging there. Heavy charged particles are understood to be charged particles which contain at least one nucleon (proton or neutron). Such devices are used for instance in cancer therapy for irradiating tumors with protons or heavier ions, e.g. He2+ or C6+.

BACKGROUND AND SUMMARY

A known proton therapy system with a plurality of treatment stations is described in U.S. Pat. No. 4,870,287. Such multi-station systems comprise a proton accelerator, typically an isochronous cyclotron or a synchrotron for providing a proton beam. Furthermore, the known multi-station systems comprise a beam guiding system for guiding the proton beam from the proton accelerator to the various treatment stations. In addition, the known devices include so-called gantries, which allow the proton beam to impinge from different directions on the irradiation object placed isocentrically at the irradiation station. Such gantry is a pivotally mounted device, in which the proton beam arriving along the swivel axis is coupled in, and in which the proton beam is deflected away and onwards from the swivel axis by a corresponding radiation optics, such that by rotating the gantry it impinges on the irradiation station, which mostly is located on the swivel axis of the gantry, from different directions.

In the known multi-station systems, only one particle accelerator is required for a plurality of treatment stations, so that the comparatively high expenditure for great accelerator facilities is distributed over a plurality of treatment stations. On the other hand, the multitude of treatment stations increases the total costs for the facility. In addition, comparatively large areas and buildings are required for the multi-station systems, which involves high costs in particular because of the radiation protection requirements. In multi-station systems, the treatment plans of the individual treatment stations must also be adjusted to each other, as it is not possible to simultaneously irradiate at different treatment stations. This leads to the further disadvantage that a delay at one treatment station involves a delay at the other treatment stations.

Therefore, it is the object of the present invention to propose an improved irradiation device. In particular, the irradiation device of the invention should have a compact configuration and require less space, so that the investment costs can be lowered as compared to known facilities. In addition, this invention should allow to omit the matching of treatment plans at various treatment stations.

In accordance with the invention, this object is solved by an irradiation device with the features of claim 1. Preferred aspects can be taken from the sub-claims.

The irradiation device of the invention comprises a particle accelerator for providing a beam of heavy charged particles (particle beam). In accordance with the invention, the particle accelerator is mounted on a carrier pivotable about at least one axis. The carrier is part of a swivelling device, which is configured such that the particle beam directed onto the treatment station can be swivelled by rotating the carrier. For mounting on the carrier, in particular compact accelerators can be used. With the configuration of the irradiation device in accordance with the invention, a particularly compact single-station irradiation system can be realized. Mounting on the pivotable carrier allows a simplification of the beam guidance, as in particular coupling a stationary beam into the swivelling device can be omitted.

The swivelling device can be configured in particular in the manner of the known gantries. The pivotable carrier then advantageously constitutes a pivotable gantry frame. The accelerator then is mounted on this gantry frame and is swivelled with the same, so that coupling an externally generated beam fixed in space into the movable gantry structure can be omitted.

In a preferred aspect, the pivotable carrier has a bent structure with at least two legs, wherein the swivel axis extends through at least two legs. With such a structure, a particularly stable swivelling device can be realized.

Furthermore, the pivotable carrier preferably has a U-shaped structure, i.e. two substantially parallel side legs with a connecting piece. Advantageously, the swivel axis extends substantially vertically through the two legs of the U-structure. Furthermore advantageously, the accelerator is mounted in the terminal portion of a leg of the U-structure. The aforementioned preferred aspects provide for a particularly favorable weight distribution, so that the swivelling device can be rotated more easily.

Another advantageous aspect consists in that one leg of the U-structure is formed with an opening and/or recess in the vicinity of the swivel axis, so that a clearance is left in this leg in the vicinity of the swivel axis for placement of the irradiation object. This configuration provides for arranging the irradiation station in the region of this leg in the vicinity of the swivel axis, so that an irradiation object positioned there can be irradiated isocentrically.

Advantageously, means for guiding and/or shaping the particle beam are mounted on the carrier. With these means, the particle beam can be guided from the accelerator to the point of emission and can be shaped, for instance focussed or expanded, in the process.

In another preferred aspect, a means for modifying or reducing the particle energy, for instance an energy degrader, is mounted on the carrier. This means can be used for varying the energy of the particles impinging on the irradiation object.

In another preferred aspect, a radiation head or nozzle with components for the controlled emission of a particle beam in the direction of the irradiation station is mounted on the carrier. Advantageously, these components comprise one or more means which are configured such that an irradiation by the pencil-beam scanning method is possible. In the pencil-beam scanning method, a volume to be irradiated in the irradiation object is raster-scanned in three dimensions. For this purpose, the particle beam is focussed on a beam cross-section which lies distinctly below the size of typical irradiation volumes. Due to the Bragg peak, the major part of the radiation dose is deposited in a depth depending on the particle energy. By using a suitably focussed pencil beam, many small volumes, so-called voxels, thus can be irradiated, so that irradiation volumes of any shape—for instance tumors—can be raster-scanned with the pencil beam in three dimensions. The shift in beam direction, i.e. depth raster scanning in the irradiation object, is achieved by varying the particle energy, mostly by using an energy degrader. The shift in the two directions vertical to the beam, i.e. raster scanning in the plane vertical to the beam, is achieved by deflection means, in particular deflection magnets. For raster scanning by the pencil-beam scanning method, the components of the nozzle therefore advantageously comprise one or more means for deflecting vertical to the particle beam and/or a means for varying the particle energy and/or a means for monitoring the beam position and/or a means for monitoring the radiation dose. With such means, a particle beam shaped like a pencil beam can be used particularly advantageously for raster scanning an irradiation object.

In another preferred aspect, a cyclotron, in particular a superconducting synchrocyclotron, is used as particle accelerator. Advantageously, a cyclotron with a strong magnetic field is chosen, which can be realized in particular with a superconducting synchrocyclotron. Due to the strong magnetic field, the cyclotron can have a particularly compact configuration. It facilitates mounting on the swivelling device and its movement. In another preferred aspect, the device at the irradiation station includes a movable patient couch for positioning irradiation patients. Particularly advantageously, the patient couch can be moved translatorily in the horizontal plane and/or be rotated. This provides for positioning an irradiation patient such that a tumor to be irradiated is located inside the irradiation region covered by the irradiation device, and the tumor can be irradiated from different directions.

In accordance with another preferred aspect, the particle accelerator provides a beam of protons and/or heavier ions, in particular He2+ or C6+, as a beam of heavy charged particles. With the different irradiation particles, different treatment results can be achieved.

An embodiment of the invention will now be explained in detail below with reference to the Figures, in which:

BRIEF DESCRIPTION OF FIGURES

FIG. 4: shows a section through a nozzle 50.

DETAILED DESCRIPTION

Figure 1:
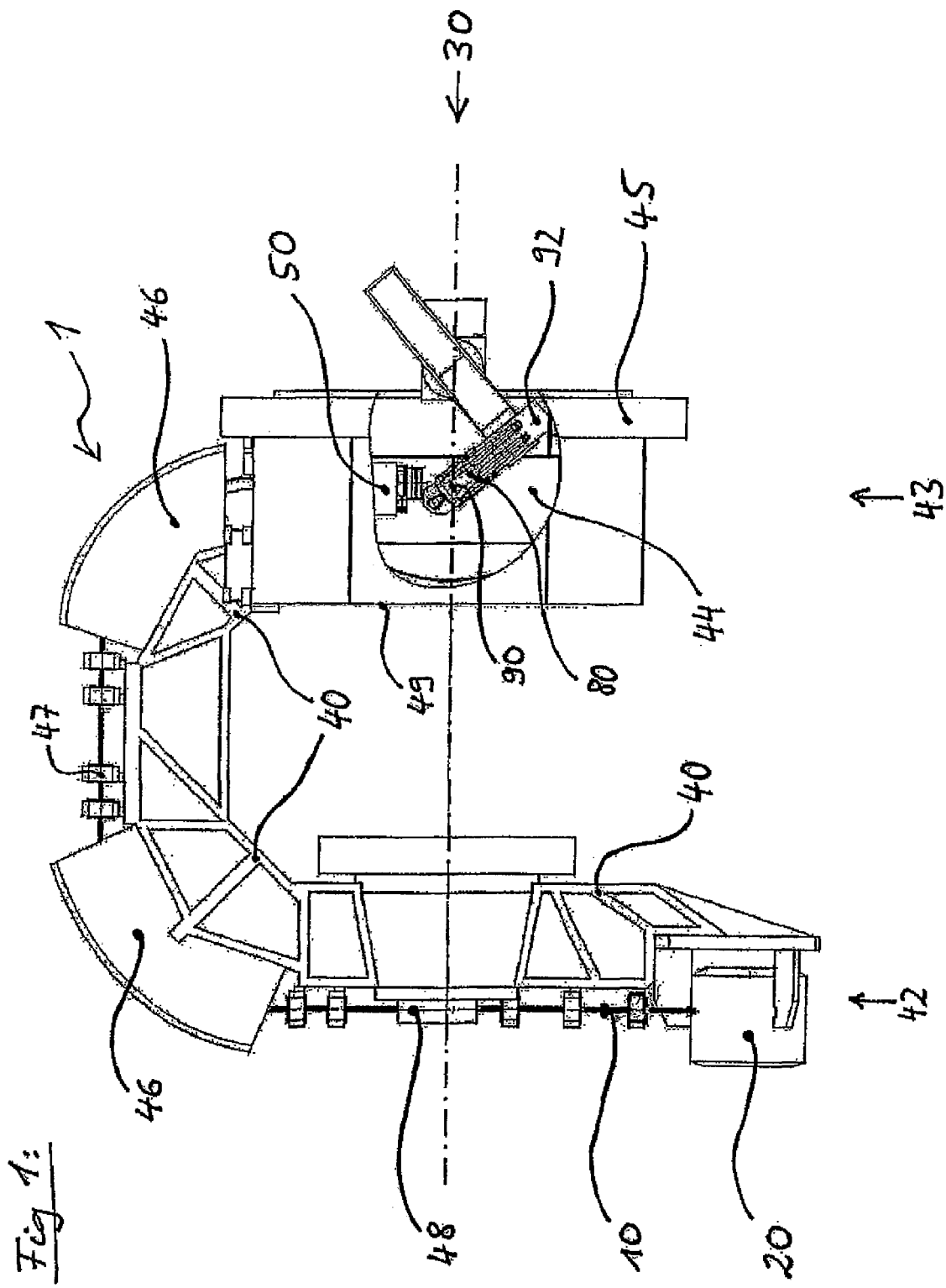
FIG. 1: shows a top view of an irradiation device 1 of the invention with a U-shaped carrier 40.

FIG. 1 shows an irradiation device 1 of the invention in a top view. The carrier 40 of the swivelling device is configured as a gantry frame 40 with a U-shaped structure. The carrier or gantry frame 40 can be swivelled about the horizontal axis 30. The swivel axis 30 extends vertically through the two legs 42, 43 of the U-structure, namely at about half the length of the legs. In the terminal region of the left leg 42, the particle accelerator 20 is mounted on the gantry frame 40. This particle accelerator is a particularly compact superconducting synchrocyclotron with a strong magnetic field. The particle accelerator provides a beam 10 of accelerated heavy charged particles, preferably protons. By using means 46 for beam guidance, the particle beam 10 is guided from the particle accelerator 20 along the U-structure of the gantry frame 40 to the nozzle 50. The means for beam guidance in particular comprise deflection magnets 46. Furthermore, focussing magnets 47 for focussing the particle beam 10 are mounted in the beam path. Alternatively or in addition, spreaders can be provided for beam expansion. In addition, an energy degrader 48 for modifying or reducing the particle energy is located in the beam path, likewise mounted on the gantry frame 40. Via the nozzle 50, the focussed particle beam or pencil beam is emitted in the direction of the irradiation station 90. In the embodiment shown in FIG. 1, the leg 43 in the vicinity of the swivel axis 30 is configured as a large ring 45, whose inner region forms a large round recess 44 whose center is located on the swivel axis. The irradiation station 90 is isocentrically arranged in the inner region 44 of the ring in the vicinity of the swivel axis. In the nozzle 50, components 52, 54, 56, 58 are located, by means of which the emission of the particle beam in the direction of the irradiation station 90 can be controlled such that an irradiation object 80 can be irradiated by the pencil-beam scanning method. These components in the nozzle 50 comprise deflection means 52, 54, in order to deflect the particle beam vertical to its direction. In particular, the deflection means can be two deflection magnets 52 and 54, which deflect the particle beam in mutually orthogonal directions. Furthermore, the means in the nozzle 50 comprise means 56 for monitoring the beam position and means 58 for monitoring the radiation dose.

Figure 2:
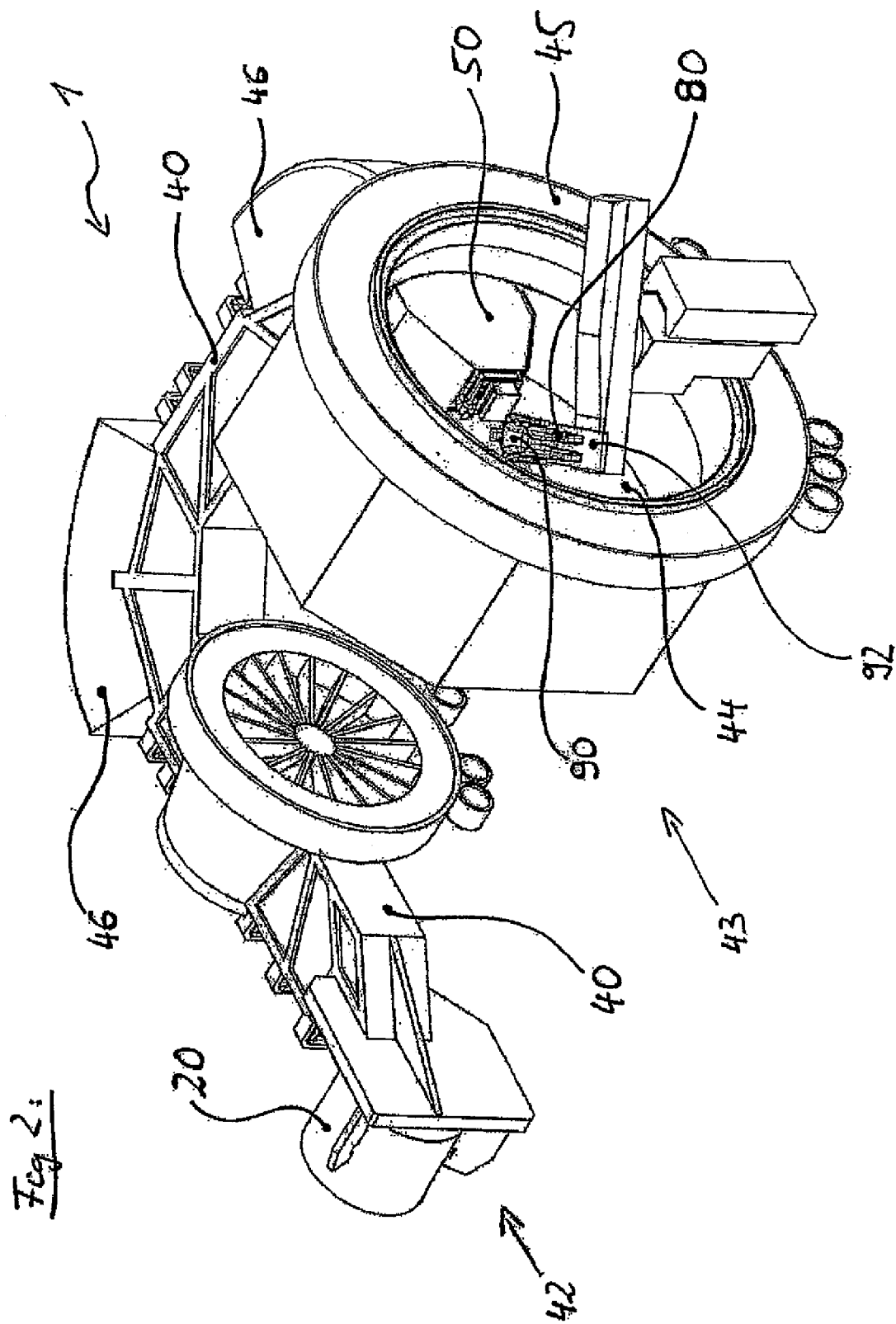
FIG. 2: shows an oblique view of a device 1 of the invention, which provides a view into the recess 44 with the irradiation station 90.

FIG. 2 shows an oblique view of the irradiation device of the invention, which provides a view into the recess 44 with the irradiation station 90. The inner region 44 of the ring 45 forms a clearance or a recess, in whose center the swivel axis is located. The irradiation station 90 is arranged in the central region of the recess 44, i.e. in the vicinity of the swivel axis. The nozzle 50, from which the particle beam is emitted in the direction of the irradiation station 90 or irradiation object 80, protrudes into the recess 44. In FIG. 2, the legs 42, 43 of the U-structure are aligned approximately horizontally. By rotating the swivelling device, the ring 45 and with it the nozzle 50 rotates such that the particle beam directed onto the irradiation station 90 or impinging on the irradiation object 80 is swivelled. In this way, the direction from which the particle beam impinges on the isocentrically arranged irradiation station 90 can be varied by rotating the swivelling device.

Figure 3:
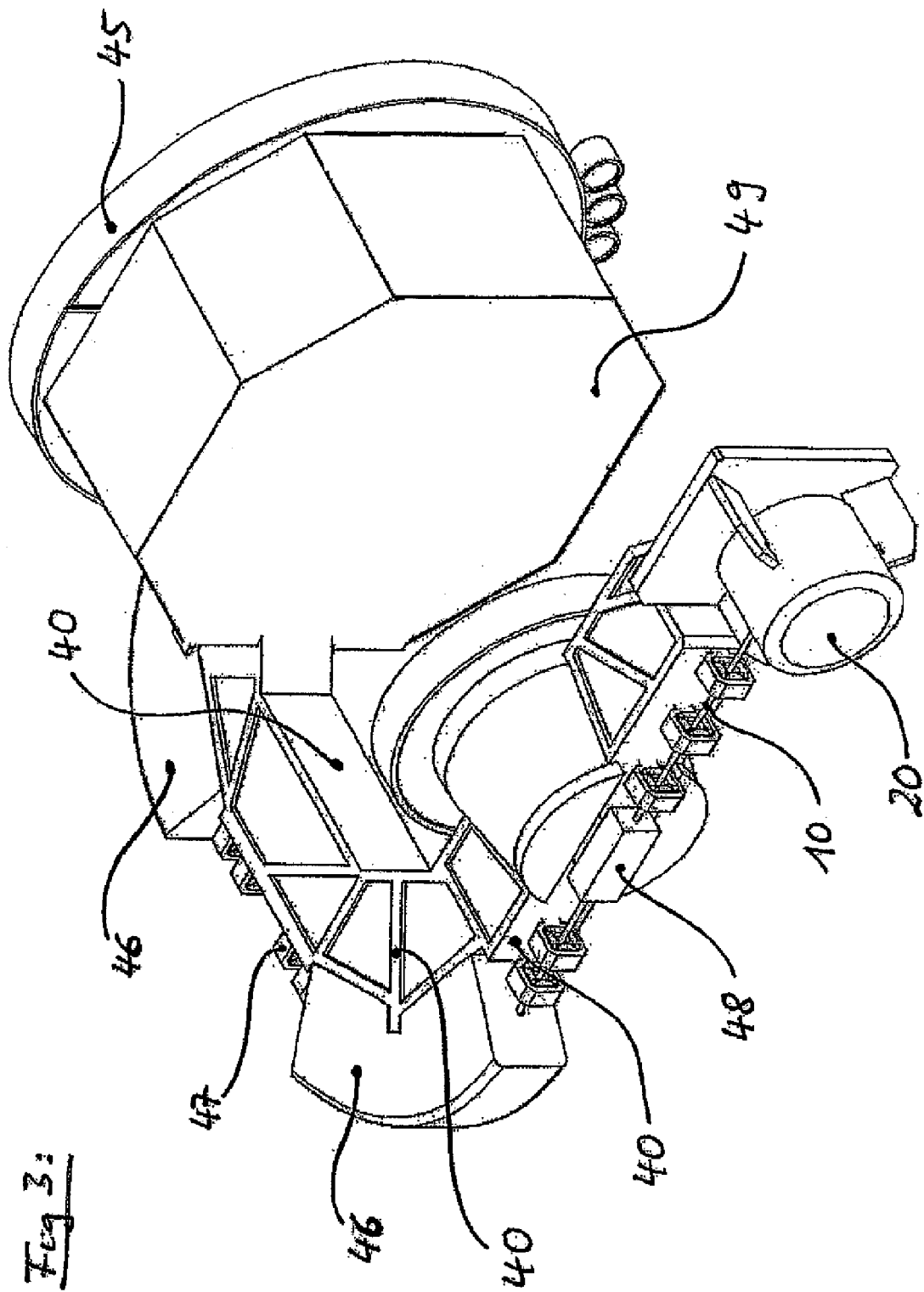
FIG. 3: shows an oblique view of a device 1 of the invention, with a view onto the rear side of the recess 44.

FIG. 3 shows an oblique view of the irradiation device of the invention, which shows the recess 44, in which the irradiation station 90 is located, from the rear. On the rear, the recess 44 is terminated by a rear wall 49.

FIG. 4 shows a detailed view of a section through the nozzle 50. The particle beam enters the nozzle at the point A and exits at the point B in the direction of the irradiation station 90. The deflection magnets 52 and 54 serve for deflection of the particle beam in directions orthogonal to the beam direction and to each other. With the means 56, 58 in the exit region of the nozzle, the beam position and the radiation dose are monitored.

As is shown in particular in FIG. 2, a movable patient couch 92 is located at the irradiation station 90, on which an irradiation patient 80 can be placed for tumor treatment. The patient couch 92 is rotatable in the horizontal plane and is also movable translatorily. In conjunction with swivelling the gantry frame 40 about the swivel axis 30, it can therefore be achieved that a tumor in the irradiation patient can be irradiated from different directions.

With the invention described above, a number of advantages are achieved. The irradiation device of the invention can be formed particularly compact, in that all components required for beam generation, guidance, shaping and control are mounted on the pivotable carrier, so that it requires comparatively little space. Furthermore, in the irradiation device of the invention it is not necessary to adjust the treatment plans of a plurality of treatment stations to each other.

The invention claimed is:

1. An irradiation device for irradiating an irradiation object with heavy charged particles at an irradiation station, comprising a particle accelerator for providing a particle beam and a swivelling device for swivelling the particle beam impinging on the irradiation object, wherein the swivelling device comprises a carrier pivotable about a swivel axis, wherein the particle accelerator is mounted on the pivotable carrier, wherein the pivotable carrier is a pivotable gantry frame, wherein the pivotable carrier has a substantially U-shaped structure with two legs, wherein the swivel axis extends substantially vertically through the two legs of the substantially U-shaped structure, wherein the particle accelerator is mounted in a terminal region of only one of the two legs of the substantially U-shaped structure, wherein another of the two legs of the substantially U-shaped structure comprises an opening and/or recess in a vicinity of the swivel axis, and wherein the irradiation station is located in a vicinity of the opening and/or recess.

2. The device according to claim 1, further comprising a particle-beam guider or shaper mounted on the carrier.

3. The device according to claim 1, further comprising a particle-energy reducer mounted on the carrier.

4. The device according to claim 1, further comprising a nozzle with nozzle components for guided and/or controlled emission of the particle beam in a direction of the irradiation station, the nozzle mounted on the carrier.

5. The device according to claim 4, wherein the nozzle components comprise one or more pencil-beam irradiation scanning components.

6. The device according to claim 4, wherein the nozzle components comprise a particle-beam deflector, a particle-beam position monitor, and/or a radiation-dose monitor.

7. The device according to claim 1, wherein the particle accelerator is a cyclotron.

8. The device according to claim 1, wherein at the irradiation station the device includes a movable patient couch for positioning irradiation patients.

9. The device according to claim 1, wherein the particle accelerator provides a beam of protons and/or heavier ions, in particular He2+ or C6+.

10. The device according to claim 1, wherein the particle accelerator is a superconducting synchrocyclotron.

11. The device according to claim 1, wherein a stationary beam is not coupled into the swivelling device.

12. An irradiation device for irradiating an irradiation object with heavy charged particles at an irradiation station, comprising:
a particle accelerator for providing a particle beam of heavy charged particles; and
a swivelling device for swivelling the particle beam impinging on the irradiation object, the swivelling device including a carrier pivotable about a swivel axis, the particle accelerator being mounted on the pivotable carrier, wherein the particle beam can be swivelled by rotating the carrier,
wherein the pivotable carrier has a substantially U-shaped structure with two legs, wherein the swivel axis extends substantially vertically through the two legs of the substantially U-shaped structure, wherein the particle accelerator is mounted in a terminal region of only one of the two legs of the substantially U-shaped structure, wherein another of the two legs of the substantially U-shaped structure comprises an opening and/or recess in a vicinity of the swivel axis, and wherein the irradiation station is located in a vicinity of the opening and/or recess.

13. The device of claim 12 wherein a stationary beam is not coupled into the swivelling device.

14. The device of claim 12 wherein the swivelling device includes a gantry frame so that the pivotable carrier constitutes a pivotable gantry frame, wherein the particle accelerator is mounted on the gantry frame and is swivelled with the gantry frame, where the particle beam is not an externally generated beam fixed in space.

15. An irradiation device for irradiating an irradiation object with heavy charged particles at an irradiation station, comprising:
a particle accelerator for providing a particle beam;
a swivelling device for swivelling the particle beam impinging on the irradiation object; and
a nozzle with nozzle components for guided and/or controlled emission of the particle beam in a direction of the irradiation station,
wherein the swivelling device comprises a carrier pivotable about a swivel axis,
wherein the particle accelerator and the nozzle are mounted on the pivotable carrier,
wherein the nozzle components comprise one or more pencil-beam irradiation scanning components, and
wherein one of the pencil-beam irradiation scanning components varies particle energy.

16. The irradiation device of claim 15, wherein one of the pencil-beam irradiation scanning components deflects vertical to the particle beam.

17. The irradiation device of claim 15, wherein one of the pencil-beam irradiation scanning components monitors particle beam position and/or one of the pencil-beam irradiation scanning components monitors radiation dose.

18. An irradiation device for irradiating an irradiation object with heavy charged particles at an irradiation station, comprising:
a particle accelerator for providing a particle beam of heavy charged particles;
a swivelling device for swivelling the particle beam impinging on the irradiation object, the swivelling device including a carrier pivotable about a swivel axis, the particle accelerator being mounted on the pivotable carrier, wherein the particle beam can be swivelled by rotating the carrier; and
a nozzle with nozzle components for guided and/or controlled emission of the particle beam in a direction of the irradiation station, the nozzle mounted on the carrier, wherein the nozzle components comprise one or more pencil-beam irradiation scanning components, and wherein one of the pencil-beam irradiation scanning components varies particle energy.

19. The irradiation device of claim 18, wherein one of the pencil-beam irradiation scanning components deflects vertical to the particle beam.

20. The irradiation device of claim 18, wherein one of the pencil-beam irradiation scanning components monitors particle beam position and/or one of the pencil-beam irradiation scanning components monitors radiation dose.

* * * * *